United States Patent [19]
Gore et al.

[11] Patent Number: 6,146,652
[45] Date of Patent: *Nov. 14, 2000

[54] PESTICIDE COMPOSITIONS

[75] Inventors: Robert Howard Gore, Southampton; Ronald Joseph Kopko, Doylestown; Warren Harvey Machleder, Blue Bell; William Dean Mathis, Doylestown; Bridget Marie Stevens, Horsham; Yan Sun, Dresher, all of Pa.

[73] Assignee: Rohm and Haas Company, Philadelphia, Pa.

[*] Notice: This patent issued on a continued prosecution application filed under 37 CFR 1.53(d), and is subject to the twenty year patent term provisions of 35 U.S.C. 154(a)(2).

[21] Appl. No.: 09/056,140

[22] Filed: Apr. 7, 1998

Related U.S. Application Data

[60] Provisional application No. 60/043,814, Apr. 14, 1997.

[51] Int. Cl.[7] .......................... A01N 25/02; A01N 25/10
[52] U.S. Cl. ...................... 424/405; 424/407; 424/409
[58] Field of Search ..................... 424/405, 407, 424/409

[56] References Cited

U.S. PATENT DOCUMENTS

| | | | |
|---|---|---|---|
| 3,131,119 | 4/1964 | Fordyce et al. | 514/483 |
| 4,351,754 | 9/1982 | Dupre | 524/445 |
| 4,470,966 | 9/1984 | Costanza et al. | 514/8 |
| 4,818,534 | 4/1989 | Levy | 424/404 |
| 4,818,536 | 4/1989 | Meyers et al. | 424/409 |
| 4,828,835 | 5/1989 | Meyers et al. | 424/409 |
| 4,983,389 | 1/1991 | Levy | 424/404 |
| 4,983,390 | 1/1991 | Levy | 424/404 |
| 4,985,251 | 1/1991 | Levy | 424/404 |
| 4,999,048 | 3/1991 | Freepons | 504/339 |
| 5,037,654 | 8/1991 | Puritch et al. | 424/405 |
| 5,089,259 | 2/1992 | Wessling et al. | 424/497 |
| 5,139,773 | 8/1992 | Tadros | 514/315 |
| 5,188,824 | 2/1993 | Wessling et al. | 424/78.1 |
| 5,425,955 | 6/1995 | Narayanan | 424/405 |
| 5,476,662 | 12/1995 | Narayanan et al. | 424/409 |
| 5,508,035 | 4/1996 | Wessling et al. | 424/405 |
| 5,672,353 | 9/1997 | Narayanan | 4/113 |
| 5,674,514 | 10/1997 | Hasslin | 424/405 |
| 5,679,366 | 10/1997 | Narayanan et al. | 424/409 |
| 5,688,743 | 11/1997 | Essinger, Jr. | 504/116 |
| 5,693,716 | 12/1997 | Bott et al. | 525/291 |
| 5,698,210 | 12/1997 | Levy | 424/406 |
| 5,698,211 | 12/1997 | Narayanan | 424/409 |
| 5,753,248 | 5/1998 | Bott et al. | 424/405 |
| 5,753,766 | 5/1998 | Bott et al. | 525/291 |
| 5,787,686 | 8/1998 | Bott et al. | 53/469 |

FOREIGN PATENT DOCUMENTS

| | | |
|---|---|---|
| 708 798 | 1/1967 | Belgium . |
| 29 05 122 | 8/1980 | Germany . |
| 41 40 928 A1 | 6/1993 | Germany . |
| 95/07613 | 3/1995 | WIPO . |
| WO 95/07613 | 3/1995 | WIPO . |
| WO 97/22247 | 6/1997 | WIPO . |
| WO 98/06780 | 2/1998 | WIPO . |

OTHER PUBLICATIONS

Small, P.A., "Some Factors Affecting the Solubility of Polymers," *Journal of Applied Chemistry*, 3, pp. 71–80, 1953.

*Primary Examiner*—Robert H. Harrison
*Attorney, Agent, or Firm*—Thomas D. Rogerson

[57] ABSTRACT

The present invention relates to pesticide compositions in which at least one of the components of the composition is a polymeric material which reduces the rate of crystallization of the pesticide active ingredient in the composition. This invention also provides a method for reducing the rate of crystallization of pesticide active ingredients and a method for controlling pests comprising applying to the pest the polymer-containing composition.

10 Claims, No Drawings

6,146,652

PESTICIDE COMPOSITIONS

This application claims benefit of Provisional Appl 60/043,814 filed Apr. 14, 1997.

The present invention relates to pesticide compositions in which at least one of the components of the composition is a polymeric material which reduces the rate of crystallization of the pesticide active ingredient in the composition. This invention also provides a method for reducing the rate of crystallization of pesticide active ingredients.

In the formulation of pesticide active ingredients, one of the major difficulties is maintaining the active ingredient in a non-crystalline form. For example, the presence of crystalline active ingredients can make preparation of some types of formulations more difficult because the crystalline structure must be reduced in order to properly formulate the active ingredient. Processes to reduce the crystalline structure of crystalline active ingredients such as milling, grinding, or dissolution in a solvent are often expensive and time consuming. Also, certain pesticide formulations cannot be prepared using some active ingredients because the active ingredient crystallizes from the formulation. It has also been observed that the efficacy of certain active ingredients is reduced when the active ingredient is present in a crystalline state. Thus, there is a continuing need for pesticide compositions in which the rate of crystallization of the active ingredient is reduced.

U.S. Pat. No. 3,131,119 discloses a class of organic solvent-soluble polymers, which possess a balance of hydrophilic and lipophilic groups, which are useful for dispersing water-insoluble metal salts of dithiocarbamic acids in oil systems. The polymers have both lipophilic and hydrophilic portions in a non-polar-polar balance and have a solubility parameter of 7.7 to 8.3.

We have discovered that such polymers, as well as related polymers with a wider range of solubility parameters, are surprisingly effective in reducing the rate of crystallization of many pesticide active ingredients. Addition of 0.01% to 40%, by weight, of the polymer to an active ingredient or formulation of the active ingredient has shown such reductions. This invention provides a pesticide composition comprising: a) one or more pesticides and b) 0.01% to 40%, by weight, of one or more oil-soluble polymers wherein the polymer has a solubility parameter of 6.9 to 9.0 and has either lipophilic or both lipophilic and hydrophilic character and wherein the pesticide is soluble in at least one of: 1) the monomers which make up the polymer; 2) oligomers of approximately the same proportional monomer unit composition as the polymer; 3) the polymer, and 4) a solution of the polymer and an organic solvent.

In a second embodiment, this invention provides a method to reduce the rate of crystallization of a pesticide comprising effectively admixing one or more pesticides with 0.01% to 40%, by weight, of one or more oil-soluble polymers wherein the polymer has a solubility parameter of 6.9 to 9.0 and has either lipophilic or both lipophilic and hydrophilic portions.

In another embodiment, this invention provides a method for controlling a pest comprising applying to the pest, a food source of the pest, or the habitat of the pest a composition comprising: a) one or more pesticides and b) 0.01% to 40%, by weight relative to the total weight of the composition, one or more oil-soluble polymers derived from at least one monoethylenically unsaturated polymerizable monomer wherein the polymer has a solubility parameter of 6.9 to 9.0 and has either lipophilic or both lipophilic and hydrophilic character and wherein the pesticide is soluble in at least one of; 1) the monomers which make up the polymer; 2) oligomers of approximately the same proportional monomer unit composition as the polymer; 3) the polymer, and 4) a solution of the polymer and an organic solvent.

The polymers of this invention are effective at concentrations of from about 0.01% to about 40% of the composition, depending upon the particular active ingredient present. Typically they reduce the rate of crystallization of the active ingredient at levels from 0.01% to 5% of the composition. Under optimal conditions they are very effective at levels of 0.01% to 2% of the composition.

The terms "pesticide" and "active ingredient" mean a chemical which is intended to mitigate a pest including insects, weeds, fungi, and related organisms. The pesticide of the compositions of this invention may be in the form of a pure active ingredient, a technical grade of the active ingredient, that is, the active ingredient in a concentration produced during typical manufacturing processes, or an active ingredient formulated with one or more agronomically acceptable carriers. The term "agronomically acceptable carrier" means any substance which can be used to aid the dispersion of the active ingredient of the composition in water, oil, or in a formulation used for controlling pests, such as a dust, without impairing the active ingredient's effectiveness and which by itself has no significant detrimental effect on the soil, equipment, desirable plants, or the agronomic environment. If desired, adjuvants such as surfactants, stabilizers, antifoam agents and antidrift agents may also be combined in the formulation. The pesticide may comprise from 0.01% to 99.9% by weight of the composition. When the pesticide is in the form of the pure active ingredient or technical grade of the active ingredient, it is desirable to maintain the percent active ingredient at as high a level as possible. When formulated, the pesticide preferably comprises 5 to 90% by weight of the pesticide composition. Preferably the pesticide has a solubility greater than one percent by weight in organic solvents at room temperature or at the temperature wherein the pesticide and the polymer are combined, when the composition includes such a solvent. Preferably, the pesticide has a melting point less than about 150° C. or, if the melting point is greater than 150° C., is stable at the melting point. Pesticides which are water soluble salts do not form stable compositions with the polymers of this invention.

For some applications, two or more pesticides may be combined in a formulation comprising the compositions of the present invention, thereby providing additional advantages and effectiveness, including fewer total pesticide applications, than if the pesticides are applied in separate compositions. When mixtures of pesticides are employed, the relative proportions of each in the composition will depend upon the relative efficacy and the desired application rate of each pesticide with respect to the pests to be treated as well as the effectiveness of the polymer chosen. Those skilled in the art will recognize that mixtures of pesticides may provide advantages such as a broader spectrum of activity than one pesticide used alone.

Examples of pesticides which can be used in the compositions of the present invention include: (1) fungicides such as, for example, (a) nitrophenol derivatives such as dinocap, binapacryl, and 2-sec-butyl-4,6-dinitrophenyl isopropyl carbonate; (b) heterocyclic structures such as captan folpet, glyodine, dithianon, thioquinox, benomyl, thiabendazole, vinolozolin, iprodione, procymidone, triadimenol, triadimefon, bitertanol, fluoroimide, triarimol, cycloheximide, ethirimol, dodemorph, dimethomorph, thifluzamide, and, quinomethionate; (c) miscellaneous halogenated fungicides such as: chloranil, dichlone, chloroneb, dichloran, and polychloronitrobenzenes; (d) fungicidal antibiotics such as: griseofulvin, kasugamycin and streptomycin; (e) miscellaneous fungicides such as: diphenyl sulfone, dodine, methoxyl, 1-thiocyano-2,4-dinitrobenzene, 1-phenylthiosemicarbazide, thiophanate-methyl, and cymoxanil; as well as acylalanines such as, furalaxyl, cyprofuram, ofurace, benalaxyl, and oxadixyl; fluazinam, flumetover, phenylbenzamide derivatives such as those disclosed in EP 578586 A1, amino acid derivatives such as valine derivatives disclosed in EP 550788 A1, methoxyacrylates such as methyl (E)-2-(2-(6-(2-cyanophenoxy) pyrimidin-4-yloxy)phenyl)-3-methoxyacrylate; benzo(1,2,3)thiadiazole-7-carbothioic acid S-methyl ester: propamocarb; imazalil; carbendazim; myclobutanil; fenbuconazole; tridemorph; pyrazophos; fenarimol; fenpiclonil; and pyrimethanil; (2) herbicides, such as, (a) carboxylic acid derivatives, including benzoic acids and their salts; phenoxy and phenyl substituted carboxylic acids and their salts; and trichloroacetic acid and its salts; (b) carbamic acid derivatives, including ethyl N,N-di(n-propyl) thiolcarbamate and pronamide; (c) substituted ureas, (d) substituted triazines, (e) diphenyl ether derivatives such as oxyfluorfen and fluoroglycofen, (f) anilides such as propanil, (g) oxyphenoxy herbicides, (h) uracils, (i) nitriles, and (j) other organic herbicides such as dithiopyr and, thiazopyr; and (3) insecticides, including acephate, aldicarb, alpha-cypermethrin, azinphos-methyl, binapacryl, buprofezin, carbaryl, carbofuran, chlorpyrifos, clofentezine, cyhexatin, cypermethrin, deltamethrin, dicofol, diflubenzuron, dimethoate, dinocap, endosulfan, endothion, esfenvalerate, ethiofencarb, ethion, ethoate-methyl, ethoprop, fenbutatin-oxide, fenoxycarb, fensulfothion, flucycloxuron, flufenoxuron, fosmethilan, hexythiazox, methamidophos, methidathion, methiocarb, methomyl, methyl parathion, mexacarbate, oxamyl, permethrin, phosalone, phosmet, promecarb, pyridaben, resmethrin, rotenone, tebufenozide, thiodicarb, triazamate, and vamidothion.

The polymers used in the composition of this invention may be either homopolymers or copolymers, including graft, block, star, random, and variable composition polymers, which are soluble in organic solvents or vegetable, mineral, or synthetic oils and which contain either lipophilic or both lipophilic and hydrophilic character. Lipophilic character is supplied by hydrocarbon groups containing an average of eight carbon atoms, preferably an average of 12 or more carbon atoms, up to 24 carbon atoms. The polymer may contain a mixture of such groups and also groups with fewer carbon atoms. In an oil based system, the polymer will preferably contain groups averaging eight carbon atoms. Hydrophilic character is supplied by ether groups, carbonyl groups, carboxylic acid groups, carboxylic ester groups, alcohol groups, amide groups, and their thio analogs, as well as amino groups. Amino and amide nitrogens may be primary, secondary, or tertiary. The nitrogen substituents may include open-chained or cyclic groups including, for example, alkyl, cycloalkyl, phenyl, benzyl, aminoalkyl, phenoxyalkyl, hydroxyalkyl, alkoxyalkyl, alkoxyethoxyethyl, alkoxypropoxypropyl, alkoxypolyethoxyethyl, benzoxyethoxyethyl, phenoxypolyethoxyethyl, or similar polyether-containing groups. The polymer may include more than one of such hydrophilic substituents.

The lipophilic character must be sufficient to ensure solubility of the polymer in an organic solvent or oil. The hydrophilic character required will depend primarily on the nature of the pesticide.

The lipophilic character of the polymer of this invention is provided by one or more of such ethylenically unsaturated monomers as, for example, methyl, butyl, hexyl, octyl, decyl, lauryl, myristyl, cetyl, stearyl, eicosyl, or tetracosyl groups in esters of acrylic, methacrylic, fumaric, maleic, or itaconic acids, or by vinyl carboxylates with alkyl groups of at least eight carbon atoms. Depending upon the particular active ingredient, polymers or copolymers from these long-chained esters by themselves may not, however, possess the necessary lipophilic/hydrophilic or polar balance. In such cases, there must also be present either in the polymerizing molecule or in the copolymer at least one additional source of polar or hydrophilic substituents, such substituents being of sufficient polarity or present in sufficient proportion to create the needed polar balance. Another class of suitable ethylenically unsaturated monomers is vinylaromatic monomers that includes, for example, styrene, α-methylstyrene, vinyltoluene, ortho-, meta- and para-methylstyrene, ethylvinylbenzene, vinylnaphthalene and vinylxylenes. The vinylaromatic monomers can also include their corresponding substituted counterparts, for example, halogenated derivatives, that is, containing one or more halogen groups, such as fluorine, chlorine or bromine; and nitro, cyano, alkoxy, haloalkyl, carbalkoxy, carboxy, amino and alkylamino derivatives. Other suitable ethylenically unsaturated monomers include ethylene and substituted ethylene monomers, for example: α-olefins such as propylene, isobutylene and long chain alkyl α-olefins (such as ($C_{10}$–$C_{20}$) alkyl α-olefins); vinyl alcohol esters such as vinyl acetate and vinyl stearate; vinyl halides such as vinyl chloride, vinyl fluoride, vinyl bromide, vinylidene chloride, vinylidene fluoride and vinylidene bromide; and vinyl nitriles such as acrylonitrile and methacrylonitrile.

A preferred class of acrylic and methacrylic acid derivatives (hereinafter "(meth)acrylic" or "(meth)acrylate" or "(meth)acrylamide") is represented by alkyl (meth) acrylates, substituted (meth)acrylates, and substituted acrylamide and substituted methacrylamide monomers. Each of the monomers can be a single monomer or a mixture having different numbers of carbon atoms in the alkyl portion. Preferably, the monomers are selected from the group consisting of ($C_1$–$C_{24}$)alkyl (meth)acrylates, hydroxy($C_2$–$C_6$) alkyl (meth)acrylates, di($C_1$–$C_6$)alkylamino($C_2$–$C_6$)alkyl (meth)acrylates and di($C_1$–$C_6$)alkylamino($C_2$–$C_6$)alkyl (meth)acrylamides. The alkyl portion of each monomer can be linear or branched.

Particularly preferred polymers useful in the present invention are the poly(meth)acrylates derived from the polymerization of alkyl (meth)acrylate monomers. Examples of the alkyl (meth)acrylate monomer where the alkyl group contains from 1 to 6 carbon atoms are methyl methacrylate (MMA), methyl and ethyl acrylate, propyl methacrylate, butyl methacrylate (BMA) and butyl acrylate (BA), isobutyl methacrylate (IBMA), hexyl and cyclohexyl methacrylate, cyclohexyl acrylate and combinations thereof. Examples of the alkyl (meth)acrylate monomer where the alkyl group contains from 7 to 15 carbon atoms are 2-ethylhexyl acrylate (EHA), 2-ethylhexyl methacrylate, octyl methacrylate, decyl methacrylate, isodecyl methacrylate (IDMA, based on branched ($C_{10}$)alkyl isomer mixture), undecyl methacrylate, dodecyl methacrylate (also known as lauryl methacrylate), tridecyl methacrylate, tetradecyl methacrylate (also known as myristyl methacrylate), pentadecyl methacrylate and combinations thereof. Also useful are: dodecyl-pentadecyl methacrylate (DPMA), a mixture of linear and branched isomers of dodecyl, tridecyl, tetradecyl and pentadecyl methacrylates; and lauryl-myristyl methacrylate (LMA), a mixture of dodecyl and tetradecyl methacrylates. The preferred alkyl methacrylates are lauryl-myristyl methacrylate, dodecyl-pentadecyl methacrylate and isodecyl methacrylate. Examples of the alkyl (meth)acrylate monomer where the alkyl group contains from 16 to 24 carbon atoms are hexadecyl methacrylate (also known as cetyl methacrylate), heptadecyl methacrylate, octadecyl methacrylate (also known as stearyl methacrylate), nonadecyl methacrylate, eicosyl methacrylate, behenyl methacrylate and combinations thereof. Also useful are: cetyl-eicosyl methacrylate (CEMA), a mixture of hexadecyl, octadecyl, and eicosyl methacrylate; and cetyl-stearyl methacrylate (SMA), a mixture of hexadecyl and octadecyl methacrylate. Preferred $C_{16}$–$C_{24}$ alkyl methacrylates are cetyl-eicosyl methacrylate and cetyl-stearyl methacrylate.

The $C_7$–$C_{24}$ alkyl (meth)acrylate monomers described above are generally prepared by standard esterification procedures using technical grades of long chain aliphatic alcohols These commercially available alcohols are mixtures of alcohols of varying chain lengths containing between 10 and 15 or 16 and 20 carbon atoms in the alkyl group. Consequently, for the purposes of this invention, alkyl (meth)acrylate is intended to include not only the individual alkyl (meth)acrylate product named, but also to include mixtures of the alkyl (meth)acrylates with a predominant amount of the particular alkyl (meth)acrylate named. The use of these commercially available alcohol mixtures to prepare (meth)acrylate esters results in the LMA, DPMA, SMA and CEMA monomer types described above. Preferred (meth)acrylic acid derivatives useful in the process of the present invention are methyl methacrylate, butyl methacrylate, isodecyl methacrylate, lauryl-myristyl methacrylate, dodecyl-pentadecyl methacrylate, cetyl-eicosyl methacrylate and cetyl-stearyl methacrylate.

For the purposes of the present invention, it is understood that copolymer compositions representing combinations of the monomers from aforementioned classes of monomers may be prepared using the processes described herein. For example, copolymers of alkyl (meth)acrylate monomers and vinylaromatic monomers, such as styrene; copolymers of alkyl (meth)acrylate monomers and substituted (meth) acrylamide monomers, such as N,N-dimethylaminopropyl methacrylamide; copolymers of alkyl (meth)acrylate monomers and monomers based on nitrogen-containing ring compounds, such as N-vinylpyrrolidone; copolymers of vinyl acetate with fumaric acid and its derivatives; and copolymers of (meth)acrylic acid and its derivatives with maleic acid and its derivatives.

Examples of monomers providing homopolymers with an effective polar balance include N-tert-dodecylaminoethyl methacrylate and N-tert-alkylaminoethyl methacrylate with the tert-alkyl group being a $C_9$–$C_{21}$ group.

These same types of monomers may also be used in forming copolymers with other comonomers whether these are lipophilic or hydrophilic in nature. Typical comonomers useful for supplying the hydrophilic balance include lower alkyl acrylates, methacrylates, itaconates, fumarates, or maleates and comparable polymerizable ethylenically unsaturated monomers in which the alkyl portion does not exceed $C_6$ and is preferably $C_1$ to $C_4$.

Alkyloxypolyethoxyethyl acrylates and methacrylates also supply polar groups. The alkyloxy group in such ether esters may be replaced with alkylamino, alkylthio, or acyloxy groups. Vinyl acetate, propionate, and butyrate are similar sources of polar ester groups for forming copolymers. Nitrogen containing groups such as amines, amides, imides, and heterocycles, may also be used to supply polarity. Typical comonomers for this purpose include dimethylaminoethyl or dimethylaminopropyl acrylates or methacrylates, acrylamide, methacrylamide, vinylpyridines, such as 2-methyl-5-vinylpyridine, or 4- or 2-vinylpyridine, N-methylolacrylamide, N-methylolmethacrylamide, or N-methylacrylamide. Comparable polar groups can be supplied by lactams which carry a vinylidene group, such as, for example, N-vinyl-2-pyrrolidinone, N-vinylpiperidinone, N-vinyl-caprolactam, and 2-pyrrolidinonylethyl methacrylate. Oxazolidine derivatives such as N-vinyloxazolidinone or N-(methacryloxloxyethyl)oxazolininone may also be used.

Examples of alkyl methacrylate and acrylate monomers with one or more hydroxyl groups in the alkyl radical, especially those where the hydroxyl group is found at the b-position (2-position) in the alkyl radical. Hydroxyalkyl methacrylate and acrylate monomers in which the substituted alkyl group is a ($C_2$–$C_6$)alkyl, branched or unbranched, are preferred. Among the hydroxy-alkyl methacrylate and acrylate monomers suitable for use in the present invention are 2-hydroxyethyl methacrylate (HEMA), 2-hydroxyethyl acrylate, 2-hydroxypropyl methacrylate, 1-methyl-2-hydroxyethyl methacrylate, 2-hydroxypropyl acrylate, 1-methyl-2-hydroxyethyl acrylate, 2-hydroxybutyl methacrylate and 2-hydroxybutyl acrylate. The preferred hydroxy-alkyl methacrylate and acrylate monomers are HEMA, 1-methyl-2-hydroxyethyl methacrylate and 2-hydroxypropyl methacrylate. A mixture of the latter two monomers is commonly referred to as "hydroxypropyl methacrylate" or HPMA, which is the more preferred hydroxyalkyl methacrylate, as are each of the components of HPMA.

The polymers and copolymers of this invention are prepared by mixing the appropriate monomers in the presence of a polymerization initiator, with or without a solvent, and optionally a chain transfer agent. The reaction can be run under agitation in an inert atmosphere at a temperature of from about 60 to 140° C. and more preferably from 115 to 125° C. Typically, the batch will exotherm to the polymerization temperature of 115–120° C. The reaction is run generally for about 4 to 10 hours or until the desired degree of polymerization has been reached. As is recognized by those skilled in the art, the time and temperature of the reaction are dependent on the choice of initiator and can be varied accordingly.

Initiators useful for this polymerization are any of the well known free-radical-producing compounds such as peroxy, hydroperoxy and azo initiators including acetyl peroxide, benzoyl peroxide, lauroyl peroxide, t-butyl peroxyiso-butyrate, caproyl peroxide, cumene hydroperoxide, 1,1-di(t-butylperoxy)-3,3,5-trimethylcyclohexane, azobisisobutyronitrile and t-butyl peroctoate. The initiator concentration is normally between 0.025 and 1% by weight based on the total weight of the monomers and more preferably from 0.05 to 0.25%. Chain transfer agents may also be added to the polymerization reaction to control the molecular weight of the polymer. When used, preferred chain transfer agents are alkyl mercaptans such as lauryl (dodecyl) mercaptan, used at a concentration of from about 0.1 to about 3% by weight.

The polymer may be prepared in the presence or absence of a solvent. Among the solvents suitable for use during the polymerization and for the preparation of concentrates are hydrocarbons, aromatic hydrocarbons, such as benzene, toluene, xylene, and aromatic naphthas, chlorinated hydrocarbons such as ethylene dichloride, esters such as ethyl propionate or butyl acetate, ketones such as N-methylpyrrolidinone, and also petroleum oils, vegetable oils and synthetic oils.

After the polymerization, the resultant polymer solution has a polymer content of between about 20 to 100% by weight. The polymer can be isolated and used directly or diluted with a solvent such as described for use in the polymerization, or the polymer or diluent solution can be used in a concentrate form. When used in the concentrate form the polymer concentration can be adjusted to any desirable level with additional diluent, for example, an organic solvent or light mineral oil. The preferred concentration of polymer in the concentrate is from 30 to 70% by weight.

The homopolymers and copolymers of this invention can be defined as those which are soluble in organic solvents or oils and which contain either lipophilic or both lipophilic and hydrophilic character. The lipophilic/hydrophilic character can be expressed in terms of the solubility parameter δ as described by Hildebrand in *Solubility of Nonelectrolytes*, 3rd Edition, Reinhold Publishing Corp., NY (1949). This value, which equals the square root of the cohesive energy density, has been determined for a wide variety of solvents and also for various polymers. See, for example, H. Burrell, *Interchemical Review*, vol. 14, No. 1, 3–16 (1955). Solubility parameters can be approximated by calculations according to the method of Small, *J. Appl. Chem.*, 3, 71, (1953). They may be determined experimentally from solubilities of polymers in a series of solvents of known δ values. The solubility parameters for copolymers can be calculated on the basis of the δ values for the units for each type of comonomer, on a weight average basis. Typical values are given in Table 1 for polymers and copolymers.

TABLE 1

Solubility Parameters of Polymers and Copolymers

| Polymer of: | δ |
| --- | --- |
| MMA | 9.5 |
| Vinyl acetate | 9.4 |
| Styrene | 9.1 |
| BMA | 9.0 |
| Hexyl MA | 8.7 |
| Octyl MA | 8.5 |
| Tert-dodecylaminoethyl MA | 8.2 |
| ViEH | 8.1 |
| LMA (72%/28%) | 8.0 |
| ViSt | 7.6 |
| Stearyl methacrylate | 7.0 |
| Dilauryl fumarate | 6.8 |
| Dicetyl itaconate | 6.5 |
| NVP | 12 |
| diMAEMA | 10 |
| 2-Methyl-5-vinyl pyridine | 10 |
| Copolymer composition (% by weight) | |
| LMA/SMA (65/35) | 7.7 |
| diLMF/NVP (80/20) | 7.8 |
| BMA/SMA (50/50) | 8.0 |
| MMA/LMA/SMA/NVP (14/51/30/5) | 8.0 |
| BMA/HMA/LMA/SMA (25/15/30/30) | 8.1 |
| BMA/LMA/SMA/diMAEMA (33.5/35/30/1.5) | 8.1 |
| ViSt/ViEH/NVP (31.6/63.2/5.2) | 8.1 |
| BMA/LMA/SMA/NVP (17/45.2/30/7.8) | 8.2 |
| BMA/LMA/SMA/NVP (32/25/35/8) | 8.3 |

MA = methacrylate
F = fumarate
NVP = N-vinyl-2-pyrrolidinone
M = methyl
B = butyl
L = lauryl-myristyl
S = cetyl-stearyl
EH = 2-ethylhexoate
Vi = vinyl
St = stearate
diMAEMA = dimethylaminoethyl methacrylate The optimum molecular weight range to obtain the greatest effectiveness of the polymer will vary depending upon the properties of the active ingredient. However, weight-average molecular weights ($M_w$) from about 10,000 to about 2,000,000 AMU (as determined by gel permeation chromatography (GPC), using poly(alkylmethacrylate) standards) are useful. Polymers with molecular weights between 15,000 and 500,000 AMU are preferred. More preferred are polymers with molecular weights between 25,000 and 100,000 AMU.

In order for the polymer to modify the rate of crystallization of the active ingredient, it is important that there be a high interaction between the active ingredient and the polymer. That is, the active ingredient molecules and the polymer molecules must be homogeneously blended together such that they interact at the molecular level. This will occur under a variety of conditions. The preferred conditions occur when: 1) the active ingredient is soluble in the monomers which make up the polymer; or 2) the active ingredient is soluble in oligomers, including dimers, trimers, and other short-chain polymers, of approximately the same proportional monomer unit composition as the polymer; or 3) the active ingredient is soluble in the polymer itself, particularly when the active ingredient is a liquid, or 4) both the active ingredient and the polymer are soluble in a cosolvent.

In addition, there are several factors which may affect the mixing of the active ingredient with the polymer including mixing temperature, presence of other components, and degree of agitation. Typically, the higher the mixing temperature, the higher the mobility of the polymer and the active ingredient. This higher mobility enhances mixing. For example, a solid technical grade active ingredient will not mix well with most polymers. However, if the system is heated to above the melting temperature of the technical, the two components often mix easily. The presence of third component, such as a solvent or solvent mixture in which both the active ingredient and the polymer are soluble, will aid in disrupting phase separations between the active ingredient and the polymer and improve mixing. Both the amount and the composition of the third component may be varied to achieve optimum results. The third component may be a mixture of a number of substances. Adding a third component is particularly important if heating the mixture of active ingredient and polymer is not a good option due to thermal instability problems with either the active ingredient or the polymer. Finally, the mechanical force (agitation rate and shear) used in the mixing process may affect the homogeneity of the mixture. Generally, increasing the degree of agitation used in the mixing process will result in enhanced mixing.

When more than one active ingredient is present in the composition, polymer choice becomes more difficult because the optimum polymer for one active ingredient may be a poor choice for the other active ingredient. However, a satisfactory compromise polymer or a mixture of different polymers may be chosen using the selection criteria above, but in addition considering the total active ingredient concentration and the ratio between the various active ingredients present in the final composition.

Although the compositions of this invention may comprise only the active ingredient and the polymer, it is preferable to dissolve the polymer, the active ingredient, or both in a solvent either prior to or during mixing. When used, the solvent may be any one or a combination of aromatic solvents, such as xylenes or xylene mixtures, toluene, benzene, or alkyl benzenes; ketones, such as cyclohexanone, methylethyl ketone, methylbutyl ketone, or methylisobutyl ketone; alcohols, such as methanol, propylene glycol, or ethylene glycol; esters, such as ethyl acetate, propyl acetate, or butyl acetate; and other organic solvents, such as dimethyl formamide, dimethyl sulfoxide, tetrahydrofuran, or N-methylpyrrolidinone. Solvent selection will depend upon the particular active ingredient and the particular polymer chosen. For example, if the active ingredient is soluble in a ketone, the appropriate polymer will be polar and also ketone soluble, such as vinyl acetate or a (meth)acrylate with a short side chain.

In addition, many of the compositions of this invention will benefit from the addition of one or more surfactants. Useful surfactants may be nonionic, anionic, cationic, or amphoteric.

Not all combinations of active ingredient and polymer will provide a composition in which the rate of crystallization of the active ingredient is reduced. However, one skilled in the formulation art will be able to select a limited group of active ingredient/polymer combinations using the above selection criteria.

For agrochemical uses, formulations of the compositions of the present invention can be applied as dusts, granulars, wettable powders, oil-based sprays, or aqueous sprays by methods commonly employed, such as conventional high-volume hydraulic sprays, low-volume sprays, air-blast, and aerial sprays. The dilution and rate of application will depend upon the type of equipment employed, the method and frequency of application desired, the pesticide application rate, and the pests to be controlled. Formulations or diluted formulations of the compositions of this invention may also contain agronomically acceptable adjuvants. Such adjuvants include surfactants, dispersants, spreaders, stickers, antifoam agents, emulsifiers, and other similar materials described in *McCutcheon's Emulsifiers and Detergents, McCutcheon's Emulsifiers and Detergents/ Functional Materials, and McCutcheo's Functional Materials*, all published annually by McCutcheon Division of MC Publishing Company (New Jersey). One advantage of reducing the rate of crystallization of the pesticide is that often formulations may be prepared which have higher concentrations of the pesticide than would be obtainable in the absence of the polymer.

The compositions of the present invention can also be mixed with fertilizers or fertilizing materials before their application. The compositions and fertilizing material can also be admixed in mixing or blending equipment, or they can be incorporated with fertilizers in granular formulations. Any relative proportion of fertilizer can be used which is suitable for the crops and weeds to be treated. The compositions of the invention will commonly comprise from 5% to 50% of the fertilizing composition. These compositions provide fertilizing materials which promote the rapid growth of desired plants, and at the same time control pests.

EXAMPLES

The following examples are provided in order to illustrate some aspects of the present invention. Unless otherwise specified, all percentages are by weight relative to the total weight of the composition.

The following general processes are used to prepare compositions of this invention:

I. Preparation of an active ingredient/polymer mixture in the absence of a solvent:

For active ingredients which are stable at or above their melting point, the active ingredient may be melted in the presence of the polymer. The active ingredient and polymer are then mixed for one to five minutes using a homogenizer, or any other kind of mixing apparatus which can provide a medium to high shear mixing rate. If necessary, the mixture may be reheated. Formulations of the active ingredient/ polymer mixture are prepared using standard formulation processes as follows:

For an emulsifiable concentrate: Dissolve the active ingredient/polymer mixture in appropriate organic solvents and surfactants under agitation.

For a wettable powder: Impregnate the active ingredient/ polymer mixture onto an inert solid carrier, then blend with other ingredients such as dispersants, surfactants, and antifoaming agents to make a wettable powder premix. Mill the premix to make the final wettable powder formulation.

For an aqueous flowable: Impregnate the active ingredient/polymer mixture onto an inert solid carrier, then blend with other ingredients such as dispersants, surfactants, biocides, antifreezing agents, antifoaming agents, thickening agents, and water. Mill this mixture to produce the final flowable formulation.

For a water dispersible granular: Prepare the dispersible granule from either the wettable powder or aqueous flowable using standard granular preparation procedures such as spray drying, pan granulation, or extrusion.

II. Preparation of an active ingedient/polymer mixture in the presence of a solvent:

For active ingredients which have a solubility greater than one percent in common organic solvents, the active ingredient and the polymer are dissolved in the chosen solvent or solvent mixture and combined. Heating the mixture or mixtures is often helpful to speed the dissolution process and to make a highly saturated solution of the active ingredient and polymer. An option for low melting active ingredients is to first melt the active ingredient and then mix it with the polymer in the chosen solvent or solvent mixture. Formulations of the active ingredient/polymer/solvent mixture are prepared using standard formulation processes as follows:

For emulsifiable concentrates: Mix the active ingredient/ polymer/solvent mixture with selected surfactants, antifoam agents, and any other components using agitation or homogenization.

For wettable powders, aqueous flowables, or water dispersible granules: Separate the active ingredient/polymer mixture from the solvent by evaporation or precipitation and then follow the processes described above.

The following examples illustrate the effect of polymers on the crystallization rate of active ingredients:

The following parameters were the key evaluation factors:

a) Visual inspection of crystallization: When neat technical was used, the rate of crystallization was quantitatively estimated by the color and physical state change of the test material. Uncrystallized samples stayed transparent and flowable, while crystallized material typically changed into an opaque colored solid mass. The crystallization rate was recorded as the time it took for this kind of change to take place.

b) Crystal measurement in emulsifiable concentrates or organic solvent solutions: The emulsifiable concentrate or organic solution was visually examined for crystal growth or the crystals were separated from the solution and weighed.

c) Crystal weight measurement in emulsions: This procedure was used in evaluating emulsifiable concentrate formulations only. A 1% (vol.) dilution of the emulsifiable concentrate formulation with 342 ppm hot water (Army hot water) was made and let stand on bench top for a given period of time. Then the emulsion mixture was poured though a 325 mesh screen. Any solid crystals collected on the screen were washed with deionized water and dried. The weight of the crystals was measured as dry weight.

d) Degree of crystallinity measured by Differential Scanning Calorimetry (DSC): This method was used to determine the degree of crystallinity of a solid sample: the solid precipitated from organic solution, solid obtained by evaporating organic solvents and/or the solid powder prepared by impregnating a molten technical onto porous carrier.

Example 1: Reduction of the crystallization rate of oxyfluorfen technical

A 20 gram sample of oxyfluorfen (2-chloro-1-(3-ethoxy-4-nitrophenoxy)-4-trifluoromethyl-benzene) technical (72% active ingredient) in a glass vial was melted at 100° C. and then cooled to 25° C. The technical material completely crystallized within 2 hours. An identical sample was melted at 100° C. Poly-SMA, 0.5% by weight, was then added, the mixture was shaken by hand until uniformly mixed, and then heated at 100° C. for an additional 30 minutes. The technical material remained free of crystals for 24 hours and then gradually crystallized completely over the next 26 hours.

Example 2: Reduction of the crystallization of oxyyluorfen from an emulsifiable concentrate formulation The use of polymer can reduce the amount of crystal formation in water dilution significantly from an emulsifiable concentrate (EC) formulation containing 33% oxyfluorfen (95% pure) technical, alkylbenzenes (Aromatic 200™, Exxon Chemical Co.) and N-methylpyrrolidinone solvents and 8–12% ethoxylated castor oil with calcium dodecylbenzenesulfonate emulsifiers,. When the formulation alone is diluted with 342 ppm hard water to yield a 2% dilution, 0.0170 grams of oxyfluorfen crystallized out after 17 hours. Addition of 0.5% of poly-isodecylmethacrylate (poly-IDMA) into an identical formulation before the dilution is made reduces the amount of oxyfluorfen crystal formation to 0.0001 grams after 17 hours.

Example 3: Reduction of the crystallization of oxyfluorfen from organic solvents The use of polymers increases oxyfluorfen solubility in common organic solvents or organic material. At 25° C. and without polymer present, a solution containing oxyfluorfen, 50% alkylbenzenes and 30% ethoxylated trisiloxane (Silwet™ L-77, Witco Chemical Co.) can contain a maximum of 20% oxyfluorfen. With the addition of 1.0% of a 28% CEMA, 62% IDMA, 10% MMA polymer, a stable solution containing 50% oxyfluorfen, 29% Aromatic 200 and 20% Silwet L-77 can be made.

Example 4: Reduction of the crystallization of tebufenozide from an emulsion

In an EC formulation containing 5% tebufenozide, 60% alkylbenzenes and 35% ethoxylated trisiloxane, the use of polymer can reduce the amount of crystal formation in water dilution significantly. When such a formulation is diluted in 342 ppm hard water to yield a 1% dilution, 0.0532 grams of tebufenozide crystallized out after 17 hours. Addition of 0.5% of a 28% CEMA, 62% IDMA, 10% MMA polymer into a 5% EC formulation before the dilution is made reduces the amount of tebufenozide crystal formation to 0.0017 grams after 17 hours.

Example 5: Reduction of the crystallization of fenbuconazole from an emulsion

In a 15% fenbuconazole EC formulation containing alkylbenzenes as the solvent and 8–12% of calcium dodecylbenzene sulfonate with alkylphenol ethoxylate (Sponto™ 232–234, Witco Chemical Co.) emulsifiers, the use of polymer can reduce the amount of crystal formation in water dilution significantly. When such a 15% EC sample is diluted in 342 ppm hard water to yield a 1% dilution, 0.0120 grams of fenbuconazole crystallized out after 17 hours. Addition of 0.5% of poly-SMA into an identical 15% EC formulation before the dilution is made can reduce the amount of fenbuconazole crystal formation to 0.0001 grams after 17 hours.

Example 6: Reduction of the crystallization of fluoroglycofen-ethyl

The use of polymer can stop fluoroglycofen-ethyl technical from crystallizing. Technical grade fluoroglycofen-ethyl was melted at 80° C. and then cooled to 25° C. The technical material completely crystallized within 50 hours. However, when idential technical is melted with the addition of 0.5% of a 28% CEMA, 62% IDMA, 10% MMA polymer, the technical material does not crystallize even after 600 days.

In a similar manner, a variety of polymers were evaluated for their ability to reduce the crystallization time of fluoroglycofen-ethyl (93% pure technical). The results of these evaluations are as follows:

| Polymer Type | | | Days to crystallize | |
| --- | --- | --- | --- | --- |
| None Crystallizes in <3 days | Polymer ID | Ratio | 0.05 Wt. % Polymer | 0.5 Wt. % Polymer |
| Methacrylate Copolymer | CEMA/IDMA/MMA | 28/62/10 | >590 | >590 |
| Methacrylate Copolymer* | CEMA/IDMA/MMA | 28/62/10 | >590 | 345 |
| Graft Dispersant Methacrylate | CEMA/IDMA/MMA/ NVP | 30/56/10/4 | >590 | 345 |
| Graft Dispersant Methacrylate* | CEMA/IDMA/MMA/ NVP | 30/56/10/4 | >590 | 345 |
| Methacrylate Copolymer | SMA | 100 | >590 | 153 |
| Methacrylate Copolymer | SMA/LMA | 35/65 | >590 | >590 |
| Methacrylate Copolymer | SMA/LMA | 6/94 | >590 | >590 |
| Methacrylate Copolymer | CEMA/LMA | 30/70 | >590 | 571 |
| Methacrylate Copolymer | CEMA/LMA | 25/75 | >590 | >590 |

-continued

| Polymer Type | Polymer ID | Ratio | Days to crystallize | |
|---|---|---|---|---|
| None Crystallizes in <3 days | | | 0.05 Wt. % Polymer | 0.5 Wt. % Polymer |
| Mixed Methacrylate Copolymers | CEMA/LMA | 15/85(50%) | >590 | >590 |
| Dispersant Methacrylate Copolymer | SMA/LMA/HPMA | 15/65/20 | >590 | 571 |
| Hydrogenated Styrene-Isoprene | Shell Vis 260 (Shell Chemical) | | 10 | 59 |
| Isoprene Star Homopolymer | Shell Vis 50 (Shell Chemical) | | >590 | 9 |
| Olefin Copolymer | Paramins ECA 13112 (Exxon Chemical) | | >590 | 154 |
| Vinyl Acetate/Fumarate Ester | Paramins ECA 7955 (Exxon Chemical) | | >590 | >590 |
| Dispersant Olefin Copolymer | Paratone 856 (Exxon Chemical) | | 9 | 121 |

*= lower $M_w$

These data indicate that the presence of polymer, at appropriate concentrations, will significantly reduce the crystallization rate.

We claim:

1. A composition consisting essentially of:
   a) one or more pesticides; and
   b) a pesticide crystallization inhibiting effective amount of one or more oil-soluble polymers having a molecular weight of from 10,000 to 2,000,000 atomic mnass units and a solubility parameter of 6.9 to 9.0 selected from the group consisting of;
      1) polymers with lipophilic character, and
      2) polymers with both lipopliilic and hydrophilic character;
      wherein the lipophlic charactor of the polymer is derived from monomer units with hydrocarbon groups containing an average of from 8 to 24 carbon atoms selected from the group consisting of:
         i) substituted or unsubstituted ($C_1$–$C_{24}$)alkyl esters of one or more monoethylenically unsaturated monomers selected from the group consisting of acrylic, methacrylic, fumaric, maleic, and itaconic acids;
         ii) substituted or unsubstituted ($C_1$–$C_{24}$)alkyl amides of one or more monoethylenically unsaturated monomers selected from the group consisting of acrylic, methacrylic, fumaric, maleic, and itaconic acids;
         iii) α-olefins; and
         iv) vinyl alcohol esters, vinyl halides, vinyl nitriles, and vinyl carboxylates; and
      wherein each pesticide is soluble in at least one selected from the group consisting of;
         1) the monomers which make up the polymer;
         2) oligomers of approximately the same proportional monomer unit composition as the polymer;
         3) the polymer, and
         4) a solution of the polymer and an organic solvent; field wherein.

2. The composition of claim 1, wherein each polymer is soluble in one or more selected from the group consisting of: a) organic solvents; b) vegetable oils; e) mineral oils; and d) synthetic oils.

3. The composition of claim 1 wherein the lipophilic character of the oil soluble polymer is derived from monomer units selected from the group consisting of one or more of substituted or unsubstituted alkyl acrylates, alkyl methacrylates, acrylamides, and methacrylamides.

4. The composition of claim 3 wherein the monomer units are selected from the group consisting of one or more of ($C_1$–$C_{24}$)alkyl acrylates, ($C_1$–$C_{24}$)alkyl methacrylates, hydroxy($C_2$–$C_6$)alkyl acrylates, hydroxy($C_2$–$C_6$)alkyl methacrylates, di($C_1$–$C_6$)alkylamino($C_2$–$C_6$)alkyl acrylates, di($C_1$–$C_6$)alkylamino($C_2$–$C_6$)alkyl methacrylates, di($C_1$–$C_6$)alkylamino($C_2$–$C_6$)alkyl acrylamides, and di($C_1$–$C_6$)alkylamino($C_2$–$C_6$)alkyl methacrylamides.

5. The composition of claim 1 wherein the hydrophilic character of the polymer is derived from monomer units selected from the group consisting of one or more of substituted or unsubstituted ($C_1$–$C_6$)alkyl esters, ($C_1$–$C_6$) alkyl thio esters, and mono or di($C_1$–$C_6$)alkylamides of one or more monoethylenically unsaturated monomers selected from the group consisting of acrylic, methacrylic, fumaric, maleic, and itaconic acids; substituted or unsubstituted vinyl esters of ($C_1$–$C_4$)carboxylates; cyclic esters, amides, and heterocycles; and vinyl substituted amines.

6. The composition of claim 5 wherein the monomer units are selected from the group consisting of hydroxyalkyl acrylates, hydroxyalkyl methacrylates, dimethylaminoethyl and dimethylaminopropyl acrylates, dimethylaminoethyl and dimethylaminopropyl methacrylates, acrylamide, methacrylamide, substituted and unsubstituted vinylpyridines, N-methylolacrylamide, N-methylolmethacrylamide, N-methylacrylamide, N-vinyl-2-pyrrolidinone, N-vinylpiperidinone, N-vinyl-caprolactam, 2-pyrrolidinonylethyl methacrylate, N-vinyloxazolidinone and N-(methacryloxloxyethyl)oxazolininone.

7. The composition of claim 1 wherein the pesticide is selected from one or more of the group consisting of:
   (a) fungicides
   (b) herbicides; and
   (c) insecticides and miticides.

8. A method of controlling a pest comprising applying the composition of claim 1 to one or more of the group consisting of:

a) the pest, b) a food source of the pest, and c) the habitat of the pest.

9. A composition consisting essentially of the composition of claim 1 impregnated onto a solid carrier.

10. A method for reducing the rate of crystallization of a pesticide, comprising effectively homogeneously admixing the pesticide with a pesticide crystallization inhibiting effective amount of one or more oil-soluble polymers having a molecular weight of from 10,000 to 2,000,000 atomic mass units and a solubility parameter of 6.9 to 9.0 selected from the group consisting of;

1) polymers with lipophilic character, and 2) polymers with both lipophilic and hydrophilic character;

wherein the lipophilic character of the polymer is derived from monomer units with hydrocarbon groups containing an average of from 8 to 24 carbon atoms selected from the group (consisting of:

i) substituted or unsubstituted $(C_1-C_{24})$alkyl esters of one or more monoethylenically unsaturated monomers selected from the group consisting of acrylic, methacrylic, fumaric, maleic, and itaconic acids;

ii) substituted or unsubstituted $(C_1-C_{24})$alkyl amides of one or more monoethylenically unsaturated monomers selected from the group consisting of acrylic, methacrylic, fumaric, maleic, and itaconic acids;

iii) α-olefins; and iv) vinyl alcohol esters, vinyl halides, vinyl nitrites, and vinyl carboxylates; and wherein each pesticide is soluble in at least one selected from the group consisting of;

1) the monomers which make up the polymer;

2) oligomers of approximately the same proportional monomer unit composition as the polymer, 3) the polymer, and 4) a solution of the polymer and an organic solvent; and wherein there is a high interaction between the pesticides and the polymer.

* * * * *